(12) United States Patent
Lindberg et al.

(10) Patent No.: US 6,322,753 B1
(45) Date of Patent: Nov. 27, 2001

(54) INTEGRATED MICROFLUIDIC ELEMENT

(75) Inventors: Peter Lindberg, Nacka; Johan Roeraade, Sågvägen 4, S-147 40 Tumba; Mårten Stjernström, Styrmansgatan 23, S-114 54 Stockholm, all of (SE); Jean Louis Viovy, Paris (FR)

(73) Assignees: Johan Roeraade, Tumba; Mårten Stjernström, Stockholm, both of (SE)

( * ) Notice: Subject to any disclaimer, the term of this patent is extended or adjusted under 35 U.S.C. 154(b) by 0 days.

(21) Appl. No.: 09/308,563

(22) PCT Filed: Jan. 23, 1998

(86) PCT No.: PCT/SE98/00102
§ 371 Date: Jun. 23, 1999
§ 102(e) Date: Jun. 23, 1999

(87) PCT Pub. No.: WO98/32535
PCT Pub. Date: Jul. 30, 1998

(30) Foreign Application Priority Data

Jan. 24, 1997 (SE) ...................................................... 9700205

(51) Int. Cl.[7] ...................................................... B01L 3/00

(52) U.S. Cl. ............................... 422/102; 156/60; 156/87; 156/99; 156/108; 216/2; 422/99; 422/104

(58) Field of Search ..................................... 422/102, 104, 422/99; 216/2; 156/60, 87, 99, 108

(56) References Cited

U.S. PATENT DOCUMENTS

| | | |
|---|---|---|
| 5,487,305 | * 1/1996 | Ristic et al. . |
| 5,593,838 | 1/1997 | Zanzucchi et al. . |
| 5,867,266 | * 2/1999 | Craighead . |
| 6,132,278 | * 10/2000 | Kang et al. . |
| 6,136,212 | * 10/2000 | Mastrangelo . |

FOREIGN PATENT DOCUMENTS

| | | |
|---|---|---|
| WO91/16966 | 11/1991 | (WO) . |
| WO93/22055 | 11/1993 | (WO) . |

OTHER PUBLICATIONS

"Electrophoresis and microlithography", R.H. Austin et al., *Analusis*, vol. 21 (1993) pp. 235–238.

"Micromachining a Miniaturized Capillary Electrophoresis–Based Chemical Analysis System on a Chip" D. Jed Harrison et al., *Science*, vol. 261 (Aug. 13, 1993) pp. 895–897.

"Glass Chips for High–Speed Capillary Electrophoresis Separations with Submicrometer Plate Heights" Carlo S. Effenhauser, *Anal. Chem.*, vol. 65 (1993) pp. 2637–2642.

"Planar Glass Chips for Capillary Electrophoresis: Repetitive Sample Injection, Quantitation and Separation Efficiency" Kurt Seiler et al., *Anal. Chem.*, vol. 65 (1993) pp. 1481–1488.

"Open Channel Electrochromatography on a Microchip" Stephen C. Jacobson, *Anal. Chem.*, vol. 66 (1994) pp. 2369–2373.

(List continued on next page.)

*Primary Examiner*—Jan Ludlow
(74) *Attorney, Agent, or Firm*—Burns, Doane, Swecker & Mathis, L.L.P.

(57) ABSTRACT

An integrated microfluidic element (1) composed of two juxtaposed plates (3, 5) bonded together, wherein at least one plate (3) has an etched structure or pattern of channels (7) on the surface facing the other plate (1) to form sealed micro channels (7), said element having micro spacers or posts (11) distributed over the etched surface of said one plate outside of said etched structure or pattern, and walls (9) surrounding said channels (7), said walls (9) having a height equal to that of said spacers or posts (11); and a method for the manufacture of such integrated microfluidic element.

23 Claims, 1 Drawing Sheet

OTHER PUBLICATIONS

"High Speed Separation of Antisense Oligonucleotides on a Micromachined Capillary Electrophoresis Device" Carlo S. Effenhauser et al., Anal. Chem., vol. 66 (1994) pp. 2949–2953.

"Electroosmotic Pumping and Valveless Control of Fluid Flow within a Manifold of Capillaries on a Glall Chip" Kurt Seiler, Anal. Chem., vol. 66 (1994) pp. 3485–3491.

"Characterization of the electrostatic bonding of silicon and Pyrex glass" A. Cozma et al., J. Micromech. Microeng., vol. 5 (1995) pp. 98–102.

"Microchip Capillary Electrophoresis with an Integrated Postcolumn Reactor" Stephen C. Jacobson et al., Anal. Chem., vol. 66 (1994) pp. 3472–3476.

"Micromachining of Capillary Electrophoresis Injectors and Separators on Glass Chips and Evaluation of Flow at Capillary Intersections" Zhonghui H. Fan et al., Anal. Chem., vol. 66 (1994) pp. 177–184.

"Integrated Capillary Electrophoresis Devices with an Efficient Postcolumn Reactor in Planar Quartz and Glass Chips" Kari Fluri et al., Anal. Chem., vol. 68 (1996) pp. 4285–4290.

"Examination of Glass–Silicon and Glass–Glass Bonding Techniques for Microfluidic Systems" N.F. Raley et al., SPIE, vol. 2639, pp. 40–45.

\* cited by examiner

INTEGRATED MICROFLUIDIC ELEMENT

The present invention relates to integrated microfluidic elements and a method for the manufacture thereof. Such elements are often composed of two juxtaposed plates bonded together, wherein one plate has an etched structure or pattern of channels on the surface facing the other plate to form sealed microchannels.

Glass substrates have in recent years been used in the manufacture of miniaturized analytic electrophoresis instrumentation with micromachining techniques (Harrison, D. J.; Fluri, K., Seiler, K.; Fan, Z.; Effenhauser, C. S.; Manz, A., *Science*, 261 (1993) 895–897. Effenhauser, C. S.; Manz, A.; Widmer, H. M., *Anal. Chem.*, 65 (1993) 2637–2642. Seiler, K.; Harrison, D. J.; Manz, A.; *Anal. Chem.*, 65 (1993) 1481–1488. Jacobson, S. C.; Hergenröder, R.; Koutny, L. B.; Ramsey, J. M., *Anal. Chem.*, 66 (1994) 2369–2373. Effenhauser, C. S.; Paulus, A.; Manz, A.; Widmer, H. M., *Anal. Chem.*, 66 (1994) 2949–2953. Seiler, K.; Fan, Z. H.; Fluri, K.; Harrison, D. J., *Anal. Chem.*, 66 (1994) 3485–3491. Jacobson, S. C.; Koutny, L. B.; Hergenroder, R.; Moore, A. W.; Ramsey, J. M., *Anal. Chem.*, 66 (1994) 3472–3476).

The insulating glass material permits the use of high voltages which can accomplish fast and efficient separations and its transparency allows for sensitive on-column optical sample detection.

Bonding of planar structures is an important step necessary in the manufacture of micro-instrumentation. For utilization of microfabricated flow channels in analytical techniques such as electrophoresis, chromatography, flow injection analysis or field-flow fractionation, the bond between the structures should preferably be direct. Thus, adhesives should be avoided that can clog the capillaries and negatively effect the efficiency or the liquid flow pattern. Accordingly, an etched structure in for example glass is by preference sealed to another glass plate by fusion bonding at a temperature that permits fusion while not deforming the glass parts, to produce uniformly assembled channel structures.

It is difficult to manufacture large bonded assemblies without irregularities, since the demand on the substrate material in terms of planarity, smoothness and cleanness increases with the area of the substrate. Furthermore, it is usually essential that the surfaces are connected under extreme clean room conditions, so that particle contamination can be eliminated at their interface. Void formation often occurs in the process cycle when bonding starts at the same time at various locations. Once a void is generated the trapped gas cannot be exhausted from its confinement.

The glass material most commonly used in micromachining laboratories is polished substrates of Pyrex Corning 7740, due to its compatibility with silicon in terms of thermal expansion. This expensive material is extensively used for anodic bonding to silicon in the manufacture of microsensors (Cozma, A.; Puers, B. *J. Micromech. Microeng.* 5 (1995) 98–102). However, details on glass-glass fusion bonding of micromachined structures are very sparse in the literature. The reported bonding process is characterized by a low yield which often involves repeated cycles ((Harrison, D. J.; Fluri, K., Seiler, K.; Fan, Z.; Effenhauser, C. S.; Manz, A., *Science*, 261 (1993) 895–897), including the use of weights placed over poorly bonded regions (Fan, Z.; Harrison, D. J. *Anal. Chem* 66 (1994) 177–184). Recently, the yield has been improved by the use of sophisticated polishing and cleaning instrumentation (Fluri, K.; Fitzpatrick, C.; Chiem, N.; Harrison, D. J. *Anal. Chem* 68 (1996) 4285–4290), available only in specialized micromachining laboratories.

For sample detection purposes, many applications require that one of the glass substrates is very thin (0.15–0.20 mm), e.g. when using high numerical aperture microscope objectives. An important example of such an application where a high degree of magnification is required is the direct observation of DNA polymer motion by fluorescence microscopy. Bonding thin glass introduces additional problems mainly due to that the commercially available thin cover glass often is manufactured by a drawing process and therefore not very planar. Raley et al. reported on a etch-back technique where first two thicker sheaths of Corning 7740 were bonded together and subsequently thinning one of the sheaths by etching and several grinding steps (Raley, N. F.; Davidson, J. C.; Balch, J. W. *Proc. SPIE-Int. Soc. Opt. Eng.* 2639 (1995) 40–45). Their best glass-glass bonding results were reported to be in the order of a 85% area coverage for 5×5 cm to 5×18 cm glass specimens with a original thickness of 800 $\mu$m. However, the etch-back technique is anticipated to depend on how well the etching process can be optimized.

The present invention has for its main object to provide new techniques for the provision of integrated microfluidic elements where the problems encountered with the prior art as illustrated above are eliminated or at least greatly reduced.

Another object of the invention is to provide a method for the manufacture of integrated microfluidic elements, wherein entrapment of gas between the plates to be bonded together can be avoided.

Yet another object of the invention is to provide a method for such manufacture, wherein the problems encountered in the bonding of two plates of different thermal coefficents of expansion together will be largely avoided.

Still another object of the invention is to provide integrated microfluidic elements free of undesirable voids and less vulnerable to inconsistencies in thermal coefficients of expansion.

For these and other objects which will be clear from the following disclosure the invention provides for a method for the manufacture of an integrated microfluidic element composed of two juxtaposed plates bonded together, wherein at least one plate has an etched structure or pattern of channels on the surface facing the other plate to form sealed microchannels. This method is characterized by forming, distributed over the etched surface of said one plate outside of said etched structure or pattern, micro spacers or posts 11, and by forming walls surrounding said channels 9, said walls 9 having a height equal to that of said spacers or posts 11 and then bonding the two plates 3, 5 together to form said element.

The plates can be bonded together by fusion bonding at an increased temperature which does not exceed the softening temperature of the plates.

The plates may also be bonded together by field assisted bonding methods. The bonding techniques used are not critical to the invention and any conventional bonding method can be used. An example of such conventional bonding method is anodic bonding of a glass plate to a silicon substrate.

The plates used can be constituted by materials used in the art, such as ordinary glass, silicon, quartz, diamond, carbon, ceramics or polymers. Particularly useful materials are glass, quartz and silicon.

It is particularly preferred in the method of the invention to form also the spacers or posts and the walls simultaneously with the forming of the structure of pattern of channels by etching.

According to an alternative method the etching can be carried out in two steps, a first step to form the channels and a second step to form the spacers or posts. By such alternative method the depth of the etched sections can be varied.

In some cases it is desired to impart special properties to the channels formed, and here the juxtaposed surfaces of the plates are covered by a thin layer before bonding the plates together. Such layer can be formed e.g. by chemical vaporization deposition (CVD), and the layer can be constituted by any desired material, such as silicon nitride, metals, glass etc.

Access to the channels formed in the microfluidic element of the invention is suitably obtained by the formation of holes in either or both of the two plates in positions coinciding with the channels.

To obtain optimal performance of the microfluidic element of the invention it is preferred that the contact surface between the plates is less than about 50% of the surface of each plate. This surface now referred to is the major side surface of the plate corresponding to the surface of the plate facing the accompanying juxtaposed plate.

The invention also provides for an integrated microfluidic element comprising two juxtaposed plates bonded together, wherein at least one plate has an etched structure or pattern of channels on the surface facing the other plate to form sealed microchannels. Such element is characterized by microspacers or posts distributed over the etched surface of said one plate outside of said etched structure or pattern, and by walls surrounding said channels. These walls have a height equal to that of said spacers or posts.

The posts or "lines" are preferably substantially equally distributed over the etched surface of the plate on areas outside of the etched structure or pattern.

The present invention as outlined above efficiently reduces or eliminates the problems associated with the prior art techniques. Thus, the use of microspacers or posts distributed over the etched surface of the plate greatly reduces the risk for the formation of voids or cracks in the plate specimens which can be due to dust particles, non-planarity and inconsistencies or differences in thermal coefficients of expansion. Furthermore, the inventive concept results in flexible structures of less built-in tension irrespective of differences in thermal coefficient of expansion of the two plates. Finally, less expensive materials can be used, such as ordinary soda-lime microslide glass which, otherwise, would be virtually impossible to use applying the conventional methods presently available.

According to a special embodiment of the invention enabling use of a variety of substrates or materials in the plates, the surfaces of the plates facing each other are coated after etching with a thin layer of quartz ($SiO_2$), such as by chemical vaporization deposition (CVD). In this manner the two plates can be joined together by conventional bonding techniques, such as fusion bonding at an increased temperature. Such method serves the double purpose of enabling easy bonding of the two plates together and simultaneously obtaining a channel lining of a uniform structure. The thickness of such quartz layer may be from fractions of a micron up to about 10 microns.

BRIEF DESCRIPTION OF THE DRAWINGS.

The invention will in the following be further described more in detail by non-limiting examples with reference to the appended drawing, wherein.

While the invention in the following will be exemplified mainly with reference to the use of glass plates for the manufacture of elements in accordance with the present invention it is to be noted that the invention is in no way limited only to the use of such glass plates but is applicable to all types of materials suitable for the intended purpose.

When using glass plates the thickness thereof can vary between about 0.1 and 1 mm, and the deptch of etching can vary between about 1 $\mu$ to about 100 $\mu$. The invention greatly facilitates the use of different materials in the two plates, such as one glass plate to be combined with a quartz or silicon plate.

EXAMPLE 1

Figure 1:
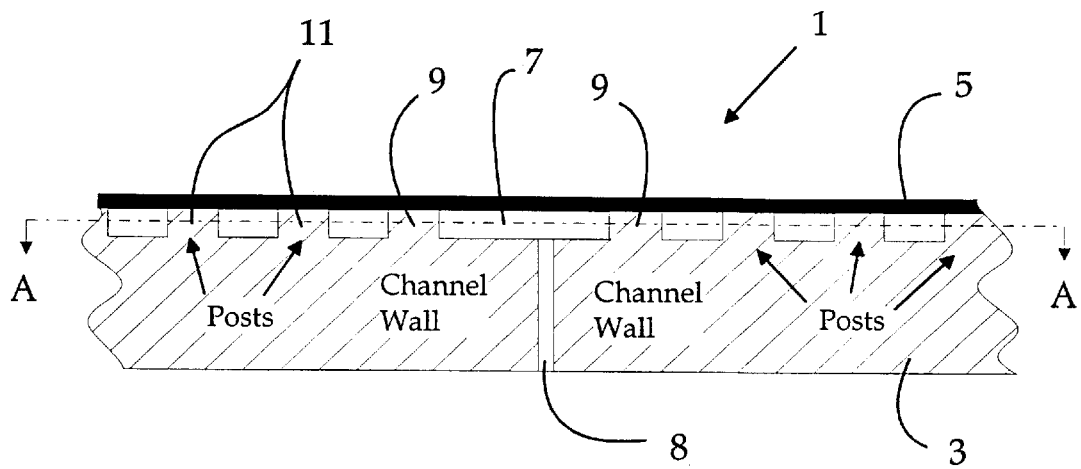
FIG. 1 is a section in sideview of an element according to the present invention.
Figure 2:
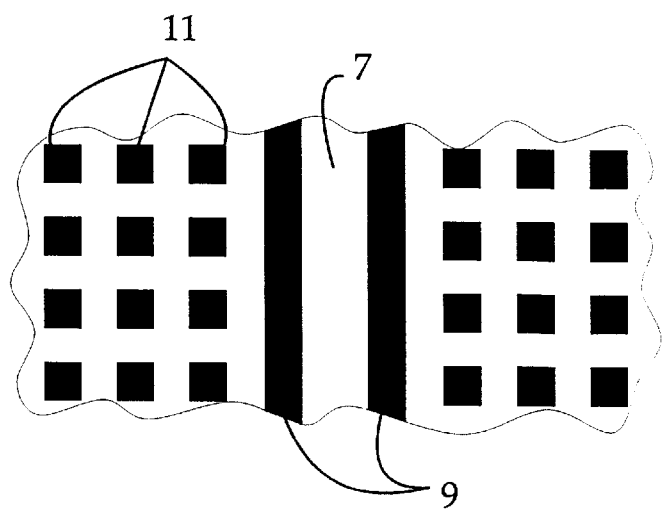
FIG. 2 is a plan view of the element of FIG. 1 taken in a plane along the line A—A in FIG. 1.

The channel manufacturing process includes the steps of: simultaneously HF etching a channel 7 and an array of posts 11 in a glass substrate 3; drilling connection holes 8 to the channel in the glass substrate 3 and bonding the formed channels 7 with a thin cover slip 5 at temperatures below the softening point of the glass (FIG. 1 and 2).

Menzel soda-lime microslide glass plates 3 (76×25 mm) with a thickness of 1 mm (±0.1 mm) were used as substrate for etching the channels (7). Cover glass plates (0.17 mm) were also obtained from Menzel. The data given by the manufacturer for the mean coefficient of thermal expansion are $90.6 \times 10^{-7}$ $K^{-1}$ and $(73-74) \times 10^{-7}$ $K^{-1}$ for the microslide and cover slips respectively. The corresponding softening points are 720° C. and 732–736° C.

The photo lithographic mask is made with an ordinary CAD program and is printed with a photo setter on a transparent film. The processing chemicals ($NH_3$, $H_2O_2$, HCl, $NH_4F$, HF, VLSI Selectipur® grade) were all obtained from Merck (Darmstadt, Germany). All processing solutions were prepared with de-ionized water from a Milli-Q system (Millipore, Bedford, Mass.) filtered through 0.2 $\mu$m filters (Millipore).

The glass substrates were first carefully cleaned in RCA-1 (5 parts distilled $H_2O$: 1 part $NH_3$ (25%): 1 $H_2O_2$ (20%)) and RCA-2 (6 parts $H_2O$: 1 part HCl (37%): 1 part $H_2O_2$ (20%)) for 10 min respectively and dehydrated in an oven (130° C.) for 20 min. For improved adherence of the photoresist, the surfaces were first primed by exposing the substrates with Microposit Primer (Shipley, Marlborough, Mass.) fumes for 3 min. The glass substrates were then coated with a positive resist (Microposit S1813 Photo Resist, Shipley) with the aid of a lint free paper and softbaked in an oven at (90° C.) for 35 min. Next, UV lithography followed by a 1 min immersion in a developing bath (Microposit Developer 351, Shipley) and cleaning in distilled $H_2O$ the UV exposed parts of the underlying glass were laid open for subsequent etching. After a hardbaking step (130° C.) for 45 min, etching was performed in a vigorously stirred aqueous mixture of 5% buffered HF (7 parts 40% $NH_4F$; 1 part 50% HF) and 9.25% conc. HCl for 45–60 min at room temperature to form channels 7, walls 9 and posts 11. The resulting etch depth was approximately 80 $\mu$m.

Connection holes 8 to the flow channel were manufactured by drilling the microslide with a carbide-drill steel (0.5 mm diameter). The remaining drilling dust was removed with ultrasonic, RCA-1 and RCA-2 rinsing steps. Bonding was performed by first carefully mating the wafers in a clean hood and placing the substrates with the cover glass downwards in an oven at 630° C. for 8 hours. In order to avoid fusion to and replication of scratches from the underlying support, plates of polished vitreous carbon were utilized (V25 grade, Le Carbone-Lorraine, Gennevilliers, France).

EXAMPLE 2

Figure 3:
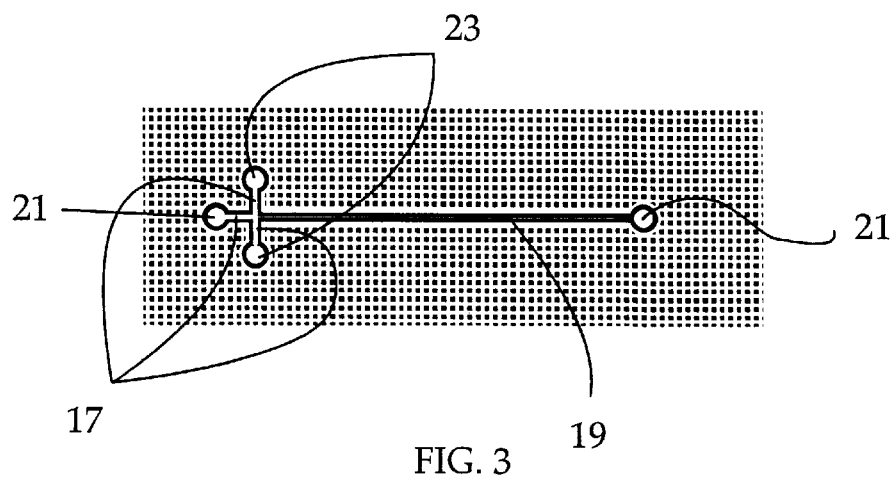
FIG. 3, is the layout of a photomask for a capillary elektrophoretic chip.

The use of the new bonding technique to manufacture microfluidic structures is illustrated in this example. The glass channel is designed for directly observing fluorescent images of individual DNA polymers undergoing separations, under a high numerical aperture microscope. The photomask used to manufacture this capillary electrophoretic chip is shown in FIG. 3 as a layout of the photomask for the capillary electrophoretic chip. The dark areas define the channel walls 9 and the posts 11 and the channel dimensions are 500 μm×3 mm for the large channels 17 and 50 μm×40 mm for the thin channel. The buffer and sample reservoirs 21,23, respectively, have a diameter of 2 mm. The square posts dimensions are 400 μm×400 μm.

The photolithographic technique presented here does not involve any advanced deposition or mask-alignment steps. The process is facilitated by using a positive resist as a direct etch mask instead of using the commonly used chromium/gold coating. The pattern in the photomask is simply transferred by UV lithography to a film of photosensitive positive resist which, in turn, by the etching process conveys the geometric shape to the glass substrate. The positive resist withstands diluted buffered HF etch solution at least up to 1 hour in room temperature, when concentrated HCl is added to the solution. This etch time is sufficient to produce deep etched channel structures in ordinary sodalime microscope slides. We observed that the lower pH also was beneficial for the etching process itself. At the used concentration of buffered HF, the smoothness of the channel walls was significantly improved in comparison with the case where no HCl addition was made. Additionally, at higher pH and HF concentrations we observed crystalline precipitates which was determined to be $CaF_2$ with EDAX.

No remaining voids or breakage after the thermal bonding step were observed when the array of posts was utilized as underpinning elements. It is suggested that the main reason for this observation is due to the fact that gases are permitted to be exhausted through the two-dimensional network of open channels. Thus, gas expansion in enclosed voids never appears when the substrates are heated. Additionally, no cracks were introduced during the bonding step due to mismatch in the thermal expansion coefficients between the etched substrate and the cover glass material. This problem is also diminished by the lattice of raised posts, since their higher degree of flexibility reduces the strain imposed on the interface between the substrates. This opens the possibility to fusion bond materials with larger difference in thermal expansion coefficients such as quartz-glass, silicon-glass etc. and broadens the choice of glass material for the anodic bonding technique (Cozma, A.; Puers, B. J. *Micromech. Microeng.* 5 (1995) 98–102), which also is performed at elevated temperatures.

It is to be observed that the present invention is not restricted to the specific embodiments described above but is broadly applicable, and the invention is not to be construed to be limited otherwise than specified in the appended patent claims.

What is claimed is:

1. A method for the manufacture of an integrated microfluidic element (5) composed of two juxtaposed plates (3, 5) bonded together, wherein at least one plate (3) has an etched structure or pattern of channels (7) on the surface facing the other plate (1) to form sealed micro channels (7), characterized by forming, distributed over the etched surface of said one plate outside of said etched structure or pattern, micro spacers or posts (11), and by forming walls (9) surrounding said channels (7), said walls (9) having a height equal to that of said spacers or posts (11) and then bonding the two plates (3, 5) together to form said element.

2. A method according to claim 1, wherein the plates (3, 5) are bonded together by fusion bonding at an increased temperature not exceeding the softening temperature of the plates.

3. A method according to claim 2, wherein the plates (3, 5) are bonded together by field-assisted bonding techniques.

4. A method according to claim 1, wherein the plates (3, 5) are constituted by materials selected from ordinary glass, quartz and silicon.

5. A method according to claim 1, wherein also said spacers or posts (11) and walls (9) are formed by etching.

6. A method according to claim 5, wherein the etching is carried out in one step to form simultaneously both channels (7) and spacers or posts (11).

7. A method according to claim 5, wherein the etching is carried out in two steps, a first step to form the channels (7) and a second step to form the spacers or posts (11).

8. A method according to claim 1, wherein the juxtaposed surfaces of the plates (3, 5) before bonding the plates together are covered by a thin layer to form a channel lining of the desired properties.

9. A method according to claim 8, wherein said thin layer is formed by chemical vaporization deposition (CVD).

10. A method according to claim 1, wherein access to the channels formed is obtained by forming holes (8) in either or both of the two plates (3, 5).

11. A method according to claim 1, wherein the contact surface between the plates (3, 5) is less than about 50% of the surface of each plate.

12. A method according to claim 1, wherein the plates (3, 5) are bonded together by field-assisted bonding techniques.

13. An integrated microfluidic element (1) composed of two juxtaposed plates (3, 5) bonded together, wherein at least one plate (3) has an etched structure or pattern of channels (7) on the surface facing the other plate (5) to form sealed micro channels (7), characterized by micro spacers or posts (11) distributed over the etched surface of said one plate outside of said etched structure or pattern, and by walls (9) surrounding said channels (7), said walls (9) having a height equal to that of said spacers or posts (11).

14. An integrated microfluid element according to claim 13, wherein the plates (3, 5) are constituted by materials selected from ordinary glass, quartz or silicon.

15. An integrated microfluid element according to claim 14, wherein the juxtaposed surfaces of the plates (3, 5) before bonding the plates together have been covered by a thin layer to give a channel lining of the desired properties.

16. An integrated microfluid element according to claim 14, wherein access to the channels is obtained by holes (8) made in either or both of the two plates (3, 5).

17. An integrated microfluid element according to claim 14, wherein the contact surface between the plates (3, 5) is less than about 50% of the surface of each plate.

18. An integrated microfluid element according to claim 13, wherein the juxtaposed surfaces of the plates (3, 5) before bonding the plates together have been covered by a thin layer to give a channel lining of the desired properties.

19. An integrated microfluid element according to claim 18, wherein access to the channels is obtained by holes (8) made in either or both of the two plates (3, 5).

20. An integrated microfluid element according to claim 18, wherein the contact surface between the plates (3, 5) is less than about 50% of the surface of each plate.

21. An integrated microfluid element according to claim 13, wherein access to the channels is obtained by holes (8) made in either or both of the two plates (3, 5).

22. An integrated microfluid element according to claim 21, wherein the contact surface between the plates (3, 5) is less than about 50% of the surface of each plate.

23. An integrated microfluid element according to claim 13, wherein the contact surface between the plates (3, 5) is less than about 50% of the surface of each plate.

* * * * *